United States Patent
Boettcher et al.

(10) Patent No.: US 6,957,622 B2
(45) Date of Patent: Oct. 25, 2005

(54) IN-SITU WEAR INDICATOR FOR NON-SELECTIVE MATERIAL REMOVAL SYSTEMS

(75) Inventors: Gregory S. Boettcher, Hopewell Junction, NY (US); Steven B. Gold, Wappingers Falls, NY (US); Robert P. Katz, Lagrangeville, NY (US); Gabriel V. Moore, Wappingers Falls, NY (US)

(73) Assignee: International Business Machiens Corporation, Armonk, NY (US)

( * ) Notice: Subject to any disclaimer, the term of this patent is extended or adjusted under 35 U.S.C. 154(b) by 0 days.

(21) Appl. No.: 10/773,605

(22) Filed: Feb. 5, 2004

(65) Prior Publication Data

US 2005/0172885 A1 Aug. 11, 2005

(51) Int. Cl.[7] .............................................. G01D 11/00
(52) U.S. Cl. ..................... 116/208; 116/200
(58) Field of Search ..................... 116/208, 212, 206, 116/200; 438/6–12; 216/59; 156/345.24, 156/345.25, 345.26, 345.27, 345.28

(56) References Cited

U.S. PATENT DOCUMENTS

| | | | |
|---|---|---|---|
| 5,947,053 A | | 9/1999 | Burnham et al. |
| 6,136,043 A | * | 10/2000 | Robinson et al. .............. 8/485 |
| 6,394,023 B1 | | 5/2002 | Crocker |
| 2003/0022397 A1 | | 1/2003 | Hess et al. |
| 2003/0040260 A1 | * | 2/2003 | Andres .......................... 451/8 |

* cited by examiner

Primary Examiner—Christopher W. Fulton
Assistant Examiner—Tania Couson
(74) Attorney, Agent, or Firm—George R. McGuire; Bond Schoeneck & King, PLLC

(57) ABSTRACT

An in-situ wear indicator for detecting wear to at least one selected part in a semiconductor manufacturing environment. The indicator is manufactured in a selected material with a selected thickness so that the indicator degrades upon exposure to the semiconductor manufacturing process at a fixed rate relative to the wear of the selected part. The indicator displays a visual indication of wear which is discernible by an automated detection device.

20 Claims, 3 Drawing Sheets

IN-SITU WEAR INDICATOR FOR NON-SELECTIVE MATERIAL REMOVAL SYSTEMS

BACKGROUND OF THE INVENTION

The invention relates to semiconductor process monitoring, and more specifically relates to an apparatus and method for determining wear indication in semiconductor manufacturing processes such ion beam etching systems and ion beam deposition systems.

The manufacture of semiconductors often includes steps that occur in an environment which causes rapid wear to the involved tooling. Examples of such systems include both deposition/implantation systems and material removal systems. The preferred embodiment of the invention that is disclosed herein is directed to a non-selective material removal system, but one skilled in the art would easily recognize that the invention could be utilized in any semiconductor manufacturing system that causes wear to the tooling in the system due to the harsh environment in certain steps of the semiconductor manufacturing system.

The tooling in the semiconductor environment includes latches and springs that are used to hold product in place so that certain materials, usually metals, can be deposited on or etched away from the product. Wear to the latches and springs causes inefficient latching that leads to an increased number of damaged products.

There are a number of non-selective material removal systems used in the processing of electrical parts such as semiconductors. The ion beam etch process is an example of one such system. The ion beam etch system removes/etches metal in a vacuum plasma environment. In non-selective material removal systems, the manufactured product is etched to provide a specific design feature using an ion beam. However, the non-selective nature of the system results in degradation to elements of the tooling of the system such as the latches on the tool stage, springs or shields. Eventually, the degradation reaches a point where the elements of the tool system need to be replaced. It has heretofore been difficult to determine the ideal or optimum replacement interval for the various elements of the system.

There are various known methods to monitor the wear in semiconductor manufacturing systems. One such method is described in U.S. Patent Application Number 2003-0022397 to Hess et al. which discloses a device that provides for a monitoring system of a through-substrate etching process by providing a sacrificial electrode in proximity to a desired etch window on the substrate. The electrical properties of the sacrificial electrode provide for the endpoint detection of wear to the substrate.

Another known method to monitor wear in semiconductor manufacturing systems is described in U.S. Pat. No. 6,394,023 to Crocker. Crocker teaches the cleaning of parts that require cleaning due to a buildup or deposition of material by utilizing a visual indicator formed in a surface that is to be subjected to a cleaning process. The visual indicator is designed into the substrate or device.

Yet another method used to monitor wear in semiconductor manufacturing systems is described in U.S. Pat. No. 5,947,053 to Burnham, et al which discloses a wear through indicator that is specific to multi-layer devices. The multi-layer device has a detecting layer designed and built into the device.

There remains a need for a wear indicator for semiconductor manufacturing systems having harsh environments where the indicator is simple, real-time, point of use and can be retrofitted to existing systems. There also remains a need for a wear indicator for semiconductor manufacturing systems that can simply and in real-time determine the ideal or optimum replacement interval for the various elements of the system. A device and/or method to meet these needs will result in lower manufacturing costs by optimizing maintenance schedules and reducing production/tooling down time.

SUMMARY OF THE INVENTION

It is an object of the present invention to provide an in-situ indicator for semiconductor manufacturing systems having harsh environments where the indicator is simple, real-time, point of use and can be used in new systems or retrofitted to existing systems.

It is another object of the invention to provide a method of simply and in real-time determining the ideal or optimum replacement interval for the various elements of a semiconductor manufacturing system.

The foregoing objects and advantages of the invention will in part be obvious and in part appear hereinafter.

These and other objects of the invention are met by the present invention which is an in-situ wear indicator for detecting wear to selected parts in a semiconductor manufacturing environment. The indicator is manufactured of a selected material with a selected thickness so that the indicator degrades upon exposure to the semiconductor manufacturing process at a known, fixed and predictable rate relative to the rate of the wear of the selected parts. The indicator displays a visual indication of wear which is discernible by an automated detection device.

DETAILED DESCRIPTION OF THE INVENTION

Although we herein describe the invention as it is used in an ion beam etch system, one skilled in the art would recognize that the invention can be used in any semiconductor manufacturing environment/process that by its nature degrades the parts of the tooling stage, including but not limited to both deposition and removal systems. The typical ion beam etch system and its many components are well known to those skilled in the art. By example, commercial ion beach etch systems are available from Veeco Instruments, Inc.

Figure 1:
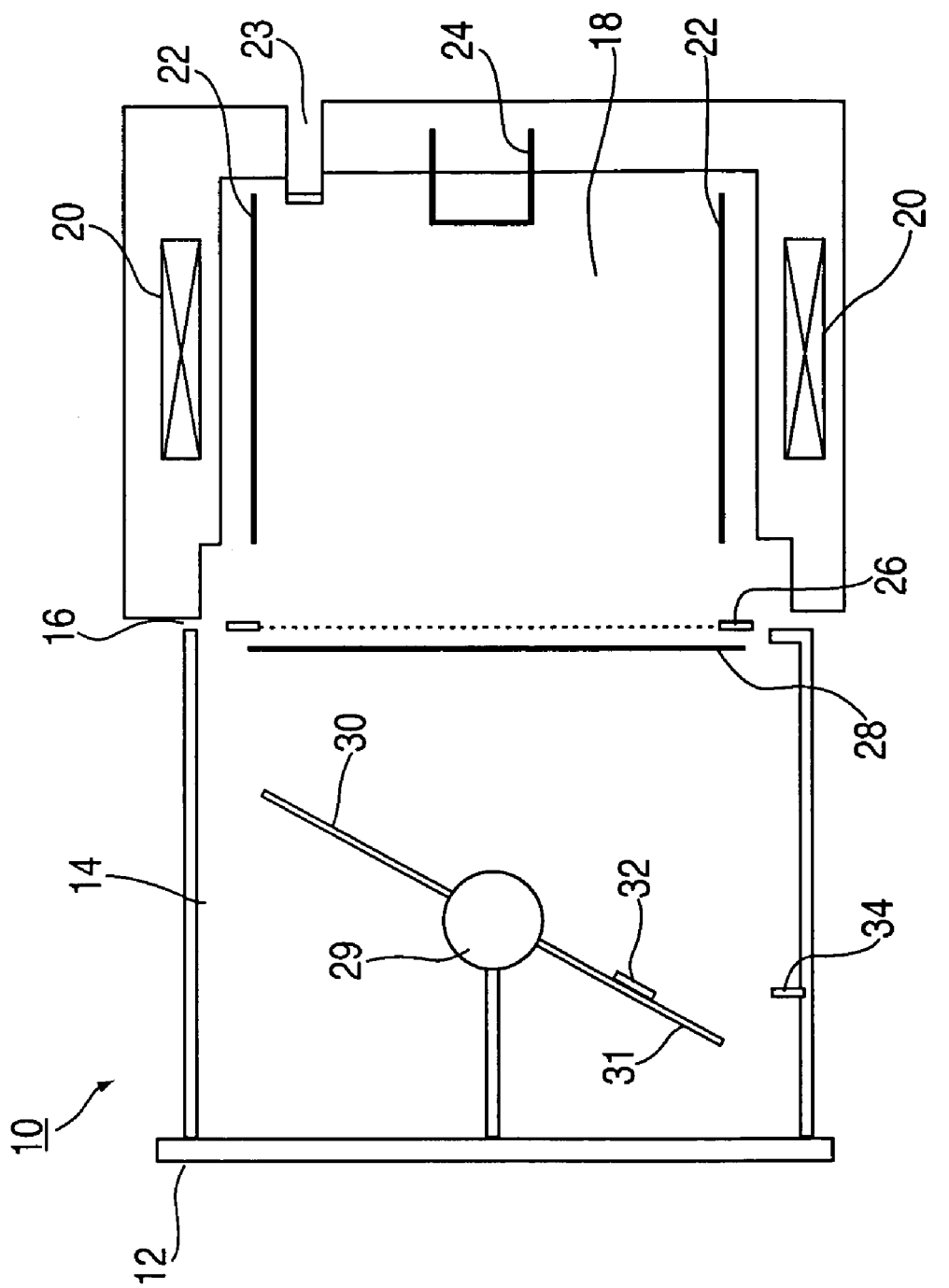
FIG. 1 is a schematic illustration of an ion beam etch chamber as embodied by the invention.

Referring now to FIG. 1, the present invention is embodied in a system 10 that includes a work chamber 14. The work chamber 14 is accessed through a chamber door 12. The work chamber 14 is connected to a discharge chamber 18 and is separated by a source flange 16. The work chamber includes a rotating fixture 29 upon which is mounted an etch stage 30. The etch stage 30 includes hold down plates 31 that are used to mount the product or substrate, which in most cases is a silicon wafer 32 or substrate.

The work chamber 14 is subjected to an ion beam which is generated within a discharge chamber 18. The discharge chamber 18 has a baffled argon gas inlet 23. The discharge chamber 18 includes a set of anodes 22 and a cathode 24. The discharge chamber 18 also includes solenoids 20 to generate magnetic fields to provide cyclodial electron paths. The discharge chamber 18 has an optically aligned grid 26 to extract a highly collimated beam (no shown). The beam passes through a neutralization filament 28 which results in a fully neutralized 10" diameter ion beam with 300 eV to 1000 eV energy.

Figure 2:
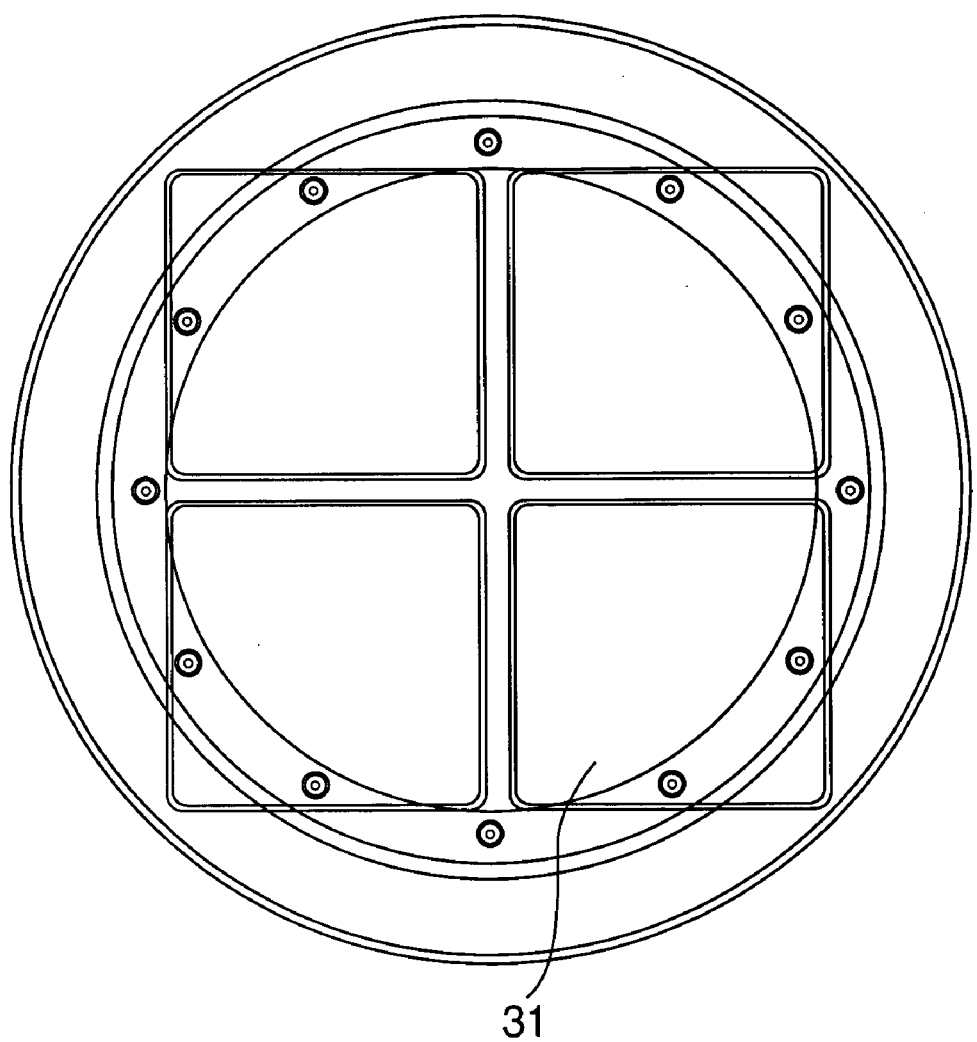
FIG. 2 is a schematic illustration of a portion of an etch stage in an ion beam etch chamber as embodied by the invention.
Figure 3A:
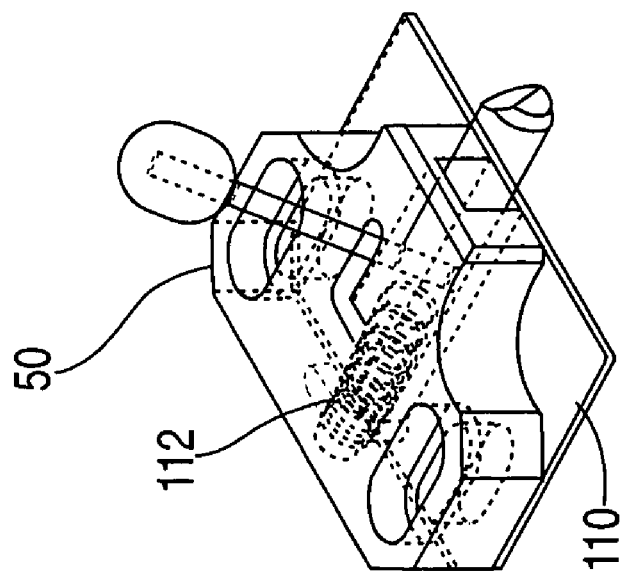
FIG. 3a is a schematic illustration of a latch product retainer portion of a tool stage in an ion beam etch system at the initial stage of use as embodied by the invention.

Referring now to FIG. 2, the semiconductor product 32 is manually loaded onto the ion beam tool stage 30 and is then secured to the tool stage 30 with the hold down plate 31 and latches 50 which serve to secure the product in proper position during the etch process. Referring now to FIG. 3a, there is shown the latch product retainer 50 that includes a spring 112 to bias the latch product retainer 50 against the product and the tooling stage 30. The spring 112 is used to secure the work product 32 to the tool stage 30 while the product 32 is being manufactured. Affixed to the tooling stage 30 and the latch product retainer 50 is an in-situ wear indicator 110. The in-situ wear indicator 110 comprises a membrane or sheath of material that is comprised of preferably the same material as the tooling or conversely is comprised of a material with known, fixed etch/wear characteristics relative to the rate of etch/wear characteristics of the tooling that is being monitored for wear.

In use, the in-situ wear indicator 110 is selected from a piece of shim stock having a relative thickness and material composition to match the characteristics of the springs or latches. The indicator 110 is placed and/or affixed to the stage 30 at the beginning of the tooling life cycle. For instance, the piece of shim stock can be placed between the latch retainer 50 and the stage 30. The ease at which the indicator 110 can be installed allows for an easy retrofit to existing systems, in that no changes need be made to the existing system in order to accommodate the piece of shim stock.

Figure 3B:
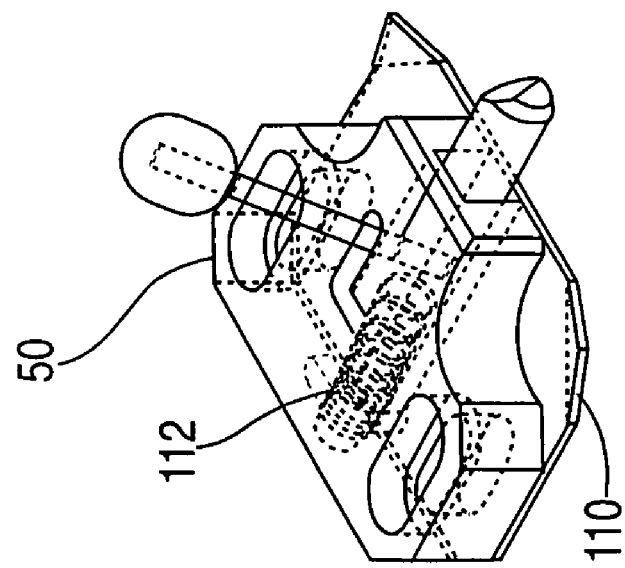
FIG. 3b is a schematic illustration of a latch product retainer portion of a tool stage in an ion beam etch system at the completed stage of use as embodied by the invention.

The system 10 is the used in the production of semiconductors by removing/etching small amounts of metal from the substrate 32 (sometimes referred to as "product" or "wafer"). The system 10 creates a plasma environment within the work chamber 14 which is non-selective and effects not only the substrate 32 but also the tooling within the system 10. After the system has been used, the wear indicator 110 becomes distorted due to the effects of the manufacturing environment. For instance, the wear indicator 110 will be begin to curl up, as indicated in FIG. 3b, which is an indication that the latch mechanisms and other exposed tooling requires service or replacement.

The visual indication of wear to the indicator 110 is detected by a laser 34 (see FIG. 1) that is mounted within the work chamber 14. One skilled in the art would recognize that there are other automated visual indicators that can be used, such as simple photo detectors and linear variable differential transformers. The operator of the system 10 is presented with a visual indication of the amount of wear that has occurred to the tooling within the work chamber 14 and can immediately begin preventive maintenance work on the system, thereby reducing system down time.

While the present invention has been disclosed in connection with the preferred embodiment, it should be understood that other embodiments may fall within the spirit and scope of the invention, as defined by the following claims.

We claim:

1. An indicator for detecting wear to at least one selected part in a semiconductor manufacturing environment, the indicator comprising:
    a selected material having a selected thickness;
    wherein said indicator degrades upon exposure to the semiconductor manufacturing environment at a fixed rate relative to the wear of the selected part; and
    wherein the indicator displays a visual indication of wear of the selected part, said
    visual indication being discernible by an automated detection device.

2. The indicator of claim 1 wherein said selected material is the same material as the selected part.

3. The indicator of claim 1 wherein said visual indication comprises a distortion in the shape of said indicator.

4. The indicator of claim 1 wherein said indicator is affixed in close proximity to the selected part on a work stage of the semiconductor manufacturing process.

5. The indicator of claim 1, wherein said selected material is selected form a group of materials that have known, fixed wear characteristics relative to the note of wear exhibited by the material composing the selected part.

6. A method for detecting wear to at least one selected part in a semiconductor manufacturing environment, the method comprising:
    providing an apparatus for processing a product comprising the at least one selected part;
    providing a wear indicator comprising a selected material having a selected thickness;
    exposing said wear indicator to the semiconductor manufacturing environment which degrades said wear indicator at a fixed rate relative to the wear of the selected part of said apparatus; and
    calculating the amount of wear to the selected part of said apparatus by examining said wear indicator with an automated detection device.

7. The method of claim 6 wherein said selected material is the same material as said selected part.

8. The method of claim 6 wherein said visual indication comprises a distortion in the shape of said indicator.

9. The method of claim 6 wherein said indicator is affixed in close proximity to the selected part on a work stage of the semiconductor manufacturing process.

10. The method of claim 6 wherein said selected material is selected from a group of materials that have known, fixed wear characteristics relative to the rate of wear exhibited by the material composing the selected part.

11. An indicator for detecting wear to at least one selected part in a non-selective material removal system, the indicator comprising:
    a selected material having selected thickness;
    wherein said indicator degrades upon exposure to the non-selective material removal system at a fixed rate relative to the wear of the selected part; and
    wherein the indicator displays a visual indication of wear to the selected part, said visual indication being discernible by an automated detection device.

12. The indicator of claim 11 wherein said selected material is the same material as the selected part.

13. The indicator of claim 11 wherein said visual indication comprises a distortion in the shape of said indicator.

14. The indicator of claim 11 wherein said indicator is affixed in close proximity to the selected part on a work stage of the material removal system.

15. The indicator of claim 11 wherein said selected material is selected from a group of material that have known, fixed wear characteristics relative to the rate of wear exhibited by the material composing the selected part.

16. A method for detecting wear to at least one selected part in a non-selective material removal system, the method comprising:
- providing an apparatus for processing a product comprising the at least one selected part;
- providing a wear indicator, comprising a selected material having a selected thickness;
- exposing said wear indicator to a non-selective material removal environment which erodes said wear indicator at a fixed rate relative to the wear of the selected parts of said apparatus;
- calculating the amount of wear to the selected part of said apparatus by examining said wear indicator with an automated detection device.

17. The method of claim 16 wherein said selected material is the same material as the selected part.

18. The method of claim 16 wherein said visual indication comprises a distortion in the shape of said indicator.

19. The method of claim 16 wherein said indicator is affixed in close proximity to the selected part on a work stage of the material removal system.

20. The method of claim 16 wherein said selected material is selected from a group of materials that have known, fixed wear characteristics relative to the rate of wear exhibited by the material composing the selected part.

* * * * *